United States Patent
Watson et al.

(10) Patent No.: US 8,463,347 B2
(45) Date of Patent: Jun. 11, 2013

(54) SYSTEMS AND METHODS FOR NORMALIZING A PLETHYSMOGRAPH SIGNAL FOR IMPROVED FEATURE ANALYSIS

(75) Inventors: James N. Watson, Dunfermline (GB); Rakesh Sethi, Vancouver (CA); Robert Stoughton, Boulder, CO (US); Paul Stanley Addison, Edinburgh (GB)

(73) Assignee: Nellcor Puritan Bennett Ireland, Galway (IE)

( * ) Notice: Subject to any disclaimer, the term of this patent is extended or adjusted under 35 U.S.C. 154(b) by 754 days.

(21) Appl. No.: 12/571,172

(22) Filed: Sep. 30, 2009

(65) Prior Publication Data
US 2011/0077486 A1    Mar. 31, 2011

(51) Int. Cl.
*A61B 5/1455* (2006.01)

(52) U.S. Cl.
USPC ............ 600/324; 600/331; 600/485; 600/475

(58) Field of Classification Search
USPC ......................................... 600/331, 485, 475
See application file for complete search history.

(56) References Cited

U.S. PATENT DOCUMENTS

| | | | |
|---|---|---|---|
| 3,835,840 A | 9/1974 | Mount | |
| 4,561,447 A | 12/1985 | Kawamura et al. | |
| 4,676,253 A | 6/1987 | Newman | |
| 4,729,382 A | 3/1988 | Schaffer | |
| 4,830,017 A | 5/1989 | Perry | |
| 4,836,213 A | 6/1989 | Wenzel et al. | |
| 4,854,327 A | 8/1989 | Kunig | |
| 4,898,176 A | 2/1990 | Petre | |
| 4,924,871 A | 5/1990 | Honeyager | |
| 4,928,700 A | 5/1990 | Harada | |
| 4,951,679 A | 8/1990 | Harada | |
| 4,976,268 A | 12/1990 | Kurosawa et al. | |
| 4,987,900 A | 1/1991 | Eckerle | |
| 5,065,765 A | 11/1991 | Eckerle | |
| 5,103,831 A | 4/1992 | Niwa | |
| 5,105,815 A | 4/1992 | Hall et al. | |
| 5,119,824 A | 6/1992 | Niwa | |
| 5,131,400 A | 7/1992 | Harada | |
| 5,163,328 A | 11/1992 | Holland | |
| 5,170,796 A | 12/1992 | Kobayashi | |
| 5,176,143 A | 1/1993 | Eckerle et al. | |
| 5,178,154 A | 1/1993 | Ackmann et al. | |

(Continued)

FOREIGN PATENT DOCUMENTS

| EP | 0443267 | 8/1991 |
|---|---|---|
| EP | 0755221 | 1/1997 |

(Continued)

OTHER PUBLICATIONS

International Search Report PCT/US2010/048591, 4 pages, mailed Feb. 16, 2011.

(Continued)

*Primary Examiner* — Michael Kahelin
*Assistant Examiner* — Mitchell Alter

(57) ABSTRACT

The present disclosure relates to systems and methods for analyzing and normalizing signals, such as PPG signals, for use in patent monitoring. The PPG signal may be detected using a continuous non-invasive blood pressure monitoring system and the normalized signals may be used to determine whether a recalibration of the system should be performed.

12 Claims, 8 Drawing Sheets

U.S. PATENT DOCUMENTS

| | | | |
|---|---|---|---|
| 5,179,956 A | 1/1993 | Harada et al. |
| 5,204,922 A | 4/1993 | Weir |
| 5,238,000 A | 8/1993 | Niwa |
| 5,241,964 A | 9/1993 | McQuilkin |
| 5,255,686 A | 10/1993 | Takeda et al. |
| 5,269,312 A | 12/1993 | Kawamura et al. |
| 5,289,823 A | 3/1994 | Eckerle |
| 5,309,917 A | 5/1994 | Wang |
| 5,431,159 A | 7/1995 | Baker |
| 5,450,852 A | 9/1995 | Archibald et al. |
| 5,467,771 A | 11/1995 | Narimatsu |
| 5,490,506 A | 2/1996 | Takatani |
| 5,494,043 A | 2/1996 | O'Sullivan et al. |
| 5,497,779 A | 3/1996 | Takaya |
| 5,505,209 A | 4/1996 | Reining |
| 5,533,511 A | 7/1996 | Kaspari |
| 5,535,753 A | 7/1996 | Petrucelli et al. |
| 5,562,621 A | 10/1996 | Claude et al. |
| 5,564,427 A | 10/1996 | Aso et al. |
| 5,575,284 A | 11/1996 | Athan |
| 5,617,868 A | 4/1997 | Harada |
| 5,640,964 A | 6/1997 | Archibald et al. |
| 5,649,542 A | 7/1997 | Archibald et al. |
| 5,649,543 A | 7/1997 | Hosaka et al. |
| 5,676,140 A | 10/1997 | Ukawa |
| 5,682,898 A | 11/1997 | Aung |
| 5,685,316 A | 11/1997 | Schookin et al. |
| 5,704,362 A | 1/1998 | Hersh et al. |
| 5,709,212 A | 1/1998 | Sugo |
| 5,720,292 A | 2/1998 | Poliac |
| 5,722,414 A | 3/1998 | Archibald et al. |
| 5,738,103 A | 4/1998 | Poliac |
| 5,743,856 A | 4/1998 | Oka et al. |
| 5,755,669 A | 5/1998 | Ono et al. |
| 5,762,610 A | 6/1998 | Narimatsu |
| 5,772,601 A | 6/1998 | Oka |
| 5,772,602 A | 6/1998 | Sakai |
| 5,776,071 A | 7/1998 | Inukai |
| 5,785,659 A | 7/1998 | Caro et al. |
| 5,791,347 A | 8/1998 | Flaherty et al. |
| 5,797,395 A | 8/1998 | Martin |
| 5,797,850 A | 8/1998 | Archibald et al. |
| 5,810,736 A | 9/1998 | Pail |
| 5,827,181 A | 10/1998 | Dias |
| 5,830,131 A | 11/1998 | Caro et al. |
| 5,832,924 A | 11/1998 | Archibald et al. |
| 5,833,618 A | 11/1998 | Caro |
| 5,848,970 A | 12/1998 | Voss |
| 5,857,975 A | 1/1999 | Golub |
| 5,873,834 A | 2/1999 | Yanagi et al. |
| 5,904,654 A | 5/1999 | Wohltmann et al. |
| 5,941,828 A | 8/1999 | Archibald et al. |
| 5,964,711 A | 10/1999 | Voss |
| 6,002,952 A | 12/1999 | Diab |
| 6,004,274 A | 12/1999 | Nolan |
| 6,007,492 A | 12/1999 | Goto et al. |
| 6,011,986 A | 1/2000 | Diab et al. |
| 6,022,320 A | 2/2000 | Ogura |
| 6,027,452 A | 2/2000 | Flaherty et al. |
| 6,027,453 A | 2/2000 | Miwa |
| 6,027,455 A | 2/2000 | Inukai et al. |
| 6,045,509 A | 4/2000 | Caro et al. |
| 6,067,462 A | 5/2000 | Diab |
| 6,083,171 A | 7/2000 | Ono et al. |
| 6,095,987 A | 8/2000 | Shmulewitz |
| 6,135,966 A | 10/2000 | Ko |
| 6,157,850 A | 12/2000 | Diab et al. |
| 6,159,157 A | 12/2000 | Archibald et al. |
| 6,161,038 A | 12/2000 | Schookin et al. |
| 6,186,954 B1 | 2/2001 | Narimatsu |
| 6,186,955 B1 | 2/2001 | Baura |
| 6,190,382 B1 | 2/2001 | Ormsby et al. |
| 6,196,974 B1 | 3/2001 | Miwa |
| 6,217,524 B1 | 4/2001 | Orr et al. |
| 6,227,196 B1 | 5/2001 | Jaffe et al. |
| 6,228,034 B1 | 5/2001 | Voss et al. |
| 6,241,661 B1 | 6/2001 | Schluess et al. |
| 6,241,679 B1 | 6/2001 | Curran |
| 6,245,022 B1 | 6/2001 | Archibald et al. |
| 6,251,081 B1 | 6/2001 | Narimatsu |
| 6,263,222 B1 | 7/2001 | Diab et al. |
| 6,292,689 B1 | 9/2001 | Wallace |
| 6,293,915 B1 | 9/2001 | Amano et al. |
| 6,299,582 B1 | 10/2001 | Brockway et al. |
| 6,332,867 B1 | 12/2001 | Chen et al. |
| 6,350,242 B1 | 2/2002 | Doten et al. |
| 6,371,921 B1 | 4/2002 | Caro |
| 6,443,905 B1 | 9/2002 | Nissila et al. |
| 6,463,311 B1 | 10/2002 | Diab |
| 6,471,646 B1 | 10/2002 | Thede |
| 6,471,655 B1 | 10/2002 | Baura |
| 6,506,161 B2 | 1/2003 | Brockway et al. |
| 6,514,211 B1 | 2/2003 | Baura |
| 6,524,240 B1 | 2/2003 | Thede |
| 6,561,986 B2 | 5/2003 | Baura |
| 6,589,185 B1 | 7/2003 | Archibald et al. |
| 6,602,199 B2 | 8/2003 | Chen et al. |
| 6,602,201 B1 | 8/2003 | Hepp et al. |
| 6,606,511 B1 | 8/2003 | Ali et al. |
| 6,626,839 B2 | 9/2003 | Doten et al. |
| 6,631,281 B1 | 10/2003 | Kastle |
| 6,645,156 B2 | 11/2003 | Oka |
| 6,658,277 B2 | 12/2003 | Wasserman |
| 6,684,090 B2 | 1/2004 | Ali et al. |
| RE38,476 E | 3/2004 | Diab et al. |
| 6,699,194 B1 | 3/2004 | Diab |
| 6,767,328 B2 | 7/2004 | Kulik |
| 6,773,397 B2 | 8/2004 | Kelly |
| 6,783,498 B2 | 8/2004 | Sackner |
| 6,816,741 B2 | 11/2004 | Diab |
| 6,822,564 B2 | 11/2004 | Al-Ali |
| 6,826,419 B2 | 11/2004 | Diab |
| 6,827,688 B2 | 12/2004 | Goto et al. |
| 6,852,083 B2 | 2/2005 | Caro |
| 6,855,112 B2 | 2/2005 | Kao |
| 6,863,652 B2 | 3/2005 | Huang et al. |
| 6,869,403 B2 | 3/2005 | Narimatsu et al. |
| 6,929,610 B2 | 8/2005 | Forstner |
| 6,996,427 B2 | 2/2006 | Ali et al. |
| 7,004,907 B2 | 2/2006 | Banet |
| 7,043,293 B1 | 5/2006 | Baura |
| 7,044,918 B2 | 5/2006 | Diab |
| 7,070,566 B2 | 7/2006 | Medero et al. |
| 7,074,192 B2 | 7/2006 | Friedman et al. |
| 7,079,035 B2 | 7/2006 | Bock et al. |
| 7,087,025 B2 | 8/2006 | Baruch |
| 7,184,809 B1 | 2/2007 | Sterling |
| 7,215,984 B2 | 5/2007 | Diab et al. |
| 7,215,986 B2 | 5/2007 | Diab et al. |
| 7,252,636 B2 | 8/2007 | Brown |
| 7,320,030 B2 | 1/2008 | Brown |
| 7,335,162 B2 | 2/2008 | Eide |
| 7,376,238 B1 | 5/2008 | Rivas et al. |
| 7,390,300 B2 | 6/2008 | Inukai |
| 7,390,301 B2 | 6/2008 | Skrabal |
| 7,393,327 B2 | 7/2008 | Inukai |
| 7,400,257 B2 | 7/2008 | Rivas |
| 7,455,643 B1 | 11/2008 | Li et al. |
| 7,481,772 B2 | 1/2009 | Banet |
| 7,485,095 B2 | 2/2009 | Shusterman |
| 7,725,187 B1 * | 5/2010 | Nabutovsky et al. ........... 607/19 |
| 2003/0036685 A1 * | 2/2003 | Goodman .................... 600/300 |
| 2005/0148885 A1 | 7/2005 | Tweed et al. |
| 2005/0251344 A1 | 11/2005 | Appel et al. |
| 2005/0261594 A1 | 11/2005 | Banet |
| 2006/0009700 A1 | 1/2006 | Brumfield et al. |
| 2006/0063992 A1 | 3/2006 | Yu et al. |
| 2006/0063993 A1 | 3/2006 | Yu et al. |
| 2006/0079945 A1 | 4/2006 | Libbus |
| 2006/0206021 A1 | 9/2006 | Diab |
| 2006/0217614 A1 | 9/2006 | Takala et al. |
| 2006/0217628 A1 | 9/2006 | Huiku |
| 2006/0241975 A1 | 10/2006 | Brown |
| 2006/0285736 A1 | 12/2006 | Brown |
| 2006/0287603 A1 | 12/2006 | Bartnik et al. |
| 2007/0043280 A1 * | 2/2007 | Mannheimer et al. ........ 600/331 |
| 2007/0066910 A1 | 3/2007 | Inukai et al. |

| | | | |
|---|---|---|---|
| 2007/0083093 | A1 | 4/2007 | Diab |
| 2007/0118045 | A1 | 5/2007 | Naghavi et al. |
| 2007/0225582 | A1 | 9/2007 | Diab et al. |
| 2007/0249467 | A1 | 10/2007 | Hong et al. |
| 2008/0015451 | A1 | 1/2008 | Hatib et al. |
| 2008/0030468 | A1 | 2/2008 | Ali et al. |
| 2008/0033305 | A1 | 2/2008 | Hatib et al. |
| 2008/0132798 | A1 | 6/2008 | Hong et al. |
| 2008/0214903 | A1 | 9/2008 | Orbach |
| 2008/0214942 | A1 | 9/2008 | Oh et al. |
| 2008/0242955 | A1 | 10/2008 | Uutela et al. |
| 2009/0048497 | A1 | 2/2009 | Keren |
| 2009/0326386 | A1 | 12/2009 | Sethi et al. |
| 2009/0326393 | A1 | 12/2009 | Sethi et al. |
| 2010/0081944 | A1 | 4/2010 | Baker et al. |
| 2011/0237914 | A1* | 9/2011 | Lamego et al. ............... 600/326 |

FOREIGN PATENT DOCUMENTS

| | | |
|---|---|---|
| GB | 2 356 250 | 5/2001 |
| GB | 2 356 251 | 5/2001 |
| GB | 2 356 252 | 5/2001 |
| JP | 03-231630 | 10/1991 |
| JP | 06-142082 | 5/1994 |
| JP | 07-136136 | 5/1995 |
| JP | 03-225268 | 12/2003 |
| WO | 2004026132 A2 | 4/2004 |

OTHER PUBLICATIONS

Bank, Alan J., Kaiser, Daniel R., "Smooth Muscle Relaxation: Effects on Arterial Compliance, Distensibility, Elastic modulus, and Pulse Wave Velocity," Hypertension, vol. 32, No. 2, Aug. 1998, pp. 356-359.

Berne, Robert M., Levy, Matthew N., eds., Physiology, 2nd edition, St. Louis, Mosby, 1988, pp. 357-681.

Finkelstein, Stanley M., Cohn, Jay N., "First- and Third-Order Models for Determining Arterial Compliance," Journal of Hypertension, vol. 10, supplement 6, Aug. 1992, pp. 511-514.

Fitchett, D., Bouthier, JD, Simon, A. Ch., Levenson, JA, Safar, ME, "Forearm Arterial Compliance: The Validation of a Plethysmographic Technique for the Measurement of Arterial Compliance," Clinical Science, vol. 67, No. 1, Jul. 1984, pp. 69-72.

Fletcher, Gerald F., ed., Cardiovascular Response to Exercise, Mt. Kisco, NY, Futura Publishing Co., 1994.

Fung, YC, Biomechanics: Circulation, 2nd Edition, New York, Springer, 1997.

Geddes, LA, Handbook of Blood Pressure Measurement, Clifton, New Jersey, Humana Press, 1991.

Millasseau, Sandrine C, Guigui, Franck G, Kelly, Ronan P., Prasad, Krishna, Cockcroft, John R., Ritter, James M., Chowienczyk, Philip J., Noninvasive Assessment of the Digital Volume Pulse: Comparison with the Peripheral Pressure Pulse, Hypertension, vol. 36, No. 6, Dec. 2000, pp. 952-956.

Moyle, John TB, Hahn, CEW, Adams, Anthony P, Pulse Oximetry, Revised Edition, London, BMJ, 1998.

Nara, Andrew R., Burns, Michael P., Downs, W. Gregory, Blood Pressure, Redmond, Washington, SpaceLabs, 1989.

Nichols, Wilmer W., O'Rourke, Michael F., McDonald's Blood Flow in Arteries: Theoretic, Experimental, and Clinical Principles, 3rd Edition, Philadelphia, Lea & Febiger, 1990.

O'Rourke, Michael F., Gallagher, David E., "Pulse Wave Analysis," Journal of Hypertension, vol. 14, supplement 5, Dec., 1996, pp. S147-S157.

Takazawa, Kenji, Tanaka, Nobuhiro, Fujita, Masami, Matsuoka, Osamu, Saiki, Tokuyu, Aikawa, Masaru, Tamura, Sinobu, Ibukiyama, Chiharu, "Assessment of Vasoactive Agents and Vascular Aging by the Second Derivative of Photoplethysmogram Waveform," Hypertension, vol. 32, No. 2, Aug. 1998, pp. 365-370.

Tardy, Y, Meister, JJ, Perret F, Brunner, HR, Arditi, M, "Non-Invasive Estimate of the Mechanical Properties of Peripheral Arteries from Ultrasonic and Photoplethysmographic Measurements," Clinical Physics and Physiological Measurement, vol. 12, No. 1, pp. 39-54, Feb. 1991.

Young, Christopher C., Mark, Jonathan B., White, William, DeBree, Ashley, Vender, Jeffery S., Fleming, Andrew, "Clinical Evaluation of Continuous Noninvasive Blood Pressure Monitoring: Accuracy and Tracking Capabilities," Journal of Clinical Monitoring, vol. 11, No. 4, Jul. 1995, pp. 245-252.

* cited by examiner

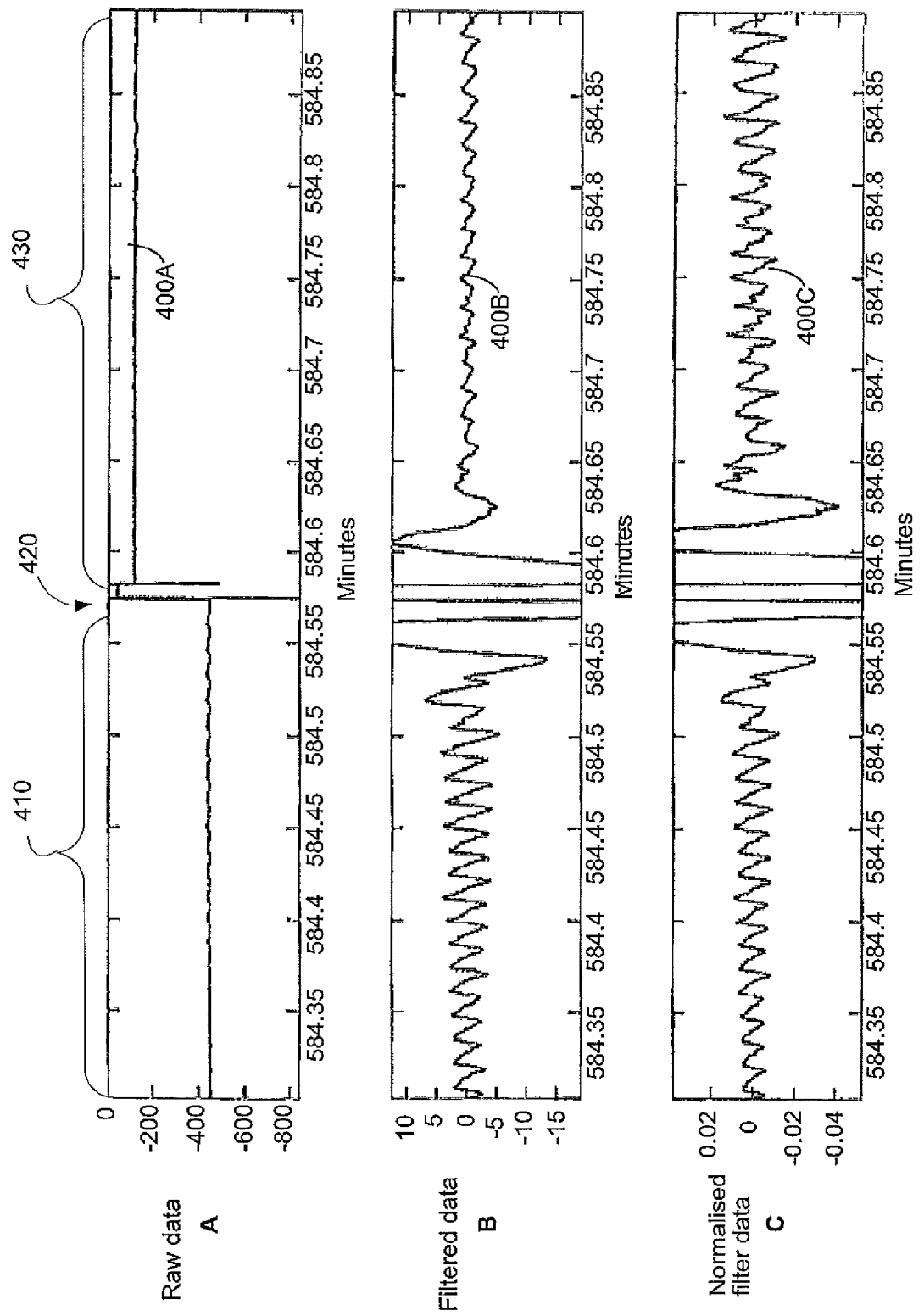

SYSTEMS AND METHODS FOR NORMALIZING A PLETHYSMOGRAPH SIGNAL FOR IMPROVED FEATURE ANALYSIS

SUMMARY

The present disclosure relates to blood pressure monitoring and, more particularly, the present disclosure relates to continuous non-invasive blood pressure monitoring.

A patient's blood pressure may be measured using a continuous non-invasive blood pressure (CNIBP) monitoring system, such as a pulse oximeter, pressure transducer, or other monitoring system. A pulse oximeter typically includes a light sensor that is placed at a site on a patient, typically a fingertip, toe, forehead or earlobe, or in the case of a neonate, across a foot. The oximeter may pass light using a light source through blood perfused tissue and photoelectrically sense the absorption of light in the tissue. For example, the oximeter may measure the intensity of light that is received at the light sensor as a function of time. A signal representing light intensity versus time or a mathematical manipulation of this signal (e.g., a scaled version thereof, a log taken thereof, a scaled version of a log taken thereof, etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof. The light intensity or the amount of light absorbed by the tissue may be used to calculate the amount of the blood constituent (e.g., oxyhemoglobin) being measured as well as the pulse rate and when each individual pulse occurs. The PPG signal used herein may also refer to other similar signals such as a signal from a pressure transducer used in certain blood pressure monitoring systems.

Multiple PPG signals may be detected using probes or sensors positioned at different points in a patient's body. For example, a first probe or sensor may be attached to the patient's ear while a second probe or sensor may be attached to the patient's finger or toe. A differential pulse transit time (DPTT) may be measured between PPG signals that can be used to compute blood pressure measurements on a continuous or periodic basis. Chen et al. U.S. Pat. No. 6,599,251, issued Jul. 29, 2003, which is hereby incorporated by reference herein in its entirety, discloses some techniques for continuous and non-invasive blood pressure monitoring using two probes or sensors that may be used in conjunction with the present disclosure.

In an embodiment, blood pressure may be computed with the use of only a single sensor or probe. In such scenarios, a time between two characteristic points of a PPG signal detected by the single sensor or probe may be measured and used in place of a DPTT to compute a patient's blood pressure. Characteristic points may be, for example, turning points in the 1st, 2nd, 3rd, or other derivative of a PPG signal. Further details on using a single probe or sensor to compute blood pressure are described in co-pending, commonly assigned U.S. patent application Ser. No. 12/242,238, entitled "Systems and Methods for Non-Invasive Blood Pressure Monitoring", filed Sep. 30, 2008, which is hereby incorporated by reference herein in its entirety.

In other embodiments, blood pressure may be computed based on the area under at least a portion of a detected PPG signal. Techniques for using area measurements to compute blood pressure are provided in co-pending, commonly assigned U.S. patent application Ser. No. 12/242,867 entitled "Systems and Methods for Non-Invasive Blood Pressure Determination", filed Sep. 30, 2008, which is hereby incorporated by reference herein in its entirety.

A pulse oximeter or other CNIBP measuring system may include a sensor or other component that may be configured to monitor signal input to optimize light intensity used by the pulse oximeter so that it is appropriate for the sensor location and monitoring conditions. For example, a sensor placed on an ear lobe may have a different optimal light intensity than that of a sensor located on a foot. In another example, changes in blood flow may also cause LED drive current settings to change, light amplitude gain changes, or servoing to occur. Optimizing the light intensity may cause the oximeter to adjust gains in an LED or other components. When light intensity is changed, the resulting PPG signal metrics, such as amplitude, or other signal characteristic may change from the PPG signal prior to the light gain change. Such a signal change may occur based on the light change alone without any change in the monitored patient's blood pressure. In some CNIBP systems, such a change to the PPG signal metric may cause the CNIBP system to recalibrate, for example as described in co-pending, commonly assigned U.S. patent application Ser. No. 12/242,858, entitled "Systems And Methods For Recalibrating A Non-Invasive Blood Pressure Monitor", filed Sep. 30, 2008, which is hereby incorporated by reference herein in its entirety. Since light gain changes and other changes may occur frequently, numerous false recalibrations may be triggered unnecessarily.

Systems and methods described herein may be directed to normalizing PPG signals following light gain or other changes, so that unnecessary recalibrations of a CNIBP monitoring system can be avoided. In an embodiment, systems and methods are provided for measuring blood pressure of a patient using a continuous non-invasive blood pressure monitoring system, in which a PPG signal is continuously detected with a sensor comprising at least one emitter and at least one detector and the sensor is coupled to a processor. The PPG signal at a second time is normalized and compared to the PPG signal at a first time. If the normalized signal and signal at the first time correspond, a blood pressure measurement may be calculated. If the normalized signal and the signal at the first time do not correspond, an alarm or a recalibration request may be generated. In an embodiment, normalization of a PPG signal may be performed when the processor determines that there is a difference in a metric of the PPG signal at the first time and the second time that exceeds a threshold.

BRIEF DESCRIPTION OF THE DRAWINGS

The above and other features of the present disclosure, its nature and various advantages will be more apparent upon consideration of the following detailed description, taken in conjunction with the accompanying drawings in which:

FIG. 4 shows illustrative PPG signals in accordance with an embodiment;

DETAILED DESCRIPTION

Some CNIBP monitoring techniques may utilize two probes or sensors positioned at two different locations on a subject's body. The elapsed time, T, between the arrivals of corresponding points of a pulse signal at the two locations may then be determined using signals obtained by the two probes or sensors. The estimated blood pressure, p, may then be related to the elapsed time, T, by $$p=a+b\cdot\ln(T) \quad (1)$$

where a and b are constants that may be dependent upon the nature of the subject and the nature of the signal detecting devices. Other suitable equations using an elapsed time between corresponding points of a pulse signal may also be used to derive an estimated blood pressure measurement. In an embodiment, a single probe or sensor may be used, in which case the variable T in equation (1) would represent the time between two characteristic points within a single detected PPG signal. In still other embodiments, the area under at least a portion of a detected PPG signal may be used to compute blood pressure instead of time.

The values of constants a and b may be determined by way of an initial calibration that uses a reference blood pressure measurement taken from the patient (e.g., using a blood pressure cuff). These constants may be adjusted responsive to a recalibration trigger, e.g., as described in co-pending, commonly assigned U.S. patent application Ser. No. 12/242,858, entitled "Systems And Methods For Recalibrating A Non-Invasive Blood Pressure Monitor", filed Sep. 30, 2008, which is hereby incorporated by reference herein in its entirety. The calibration procedure may use normalized PPG signals to determine when a recalibration should be triggered as described in detail below.

Figure 1:
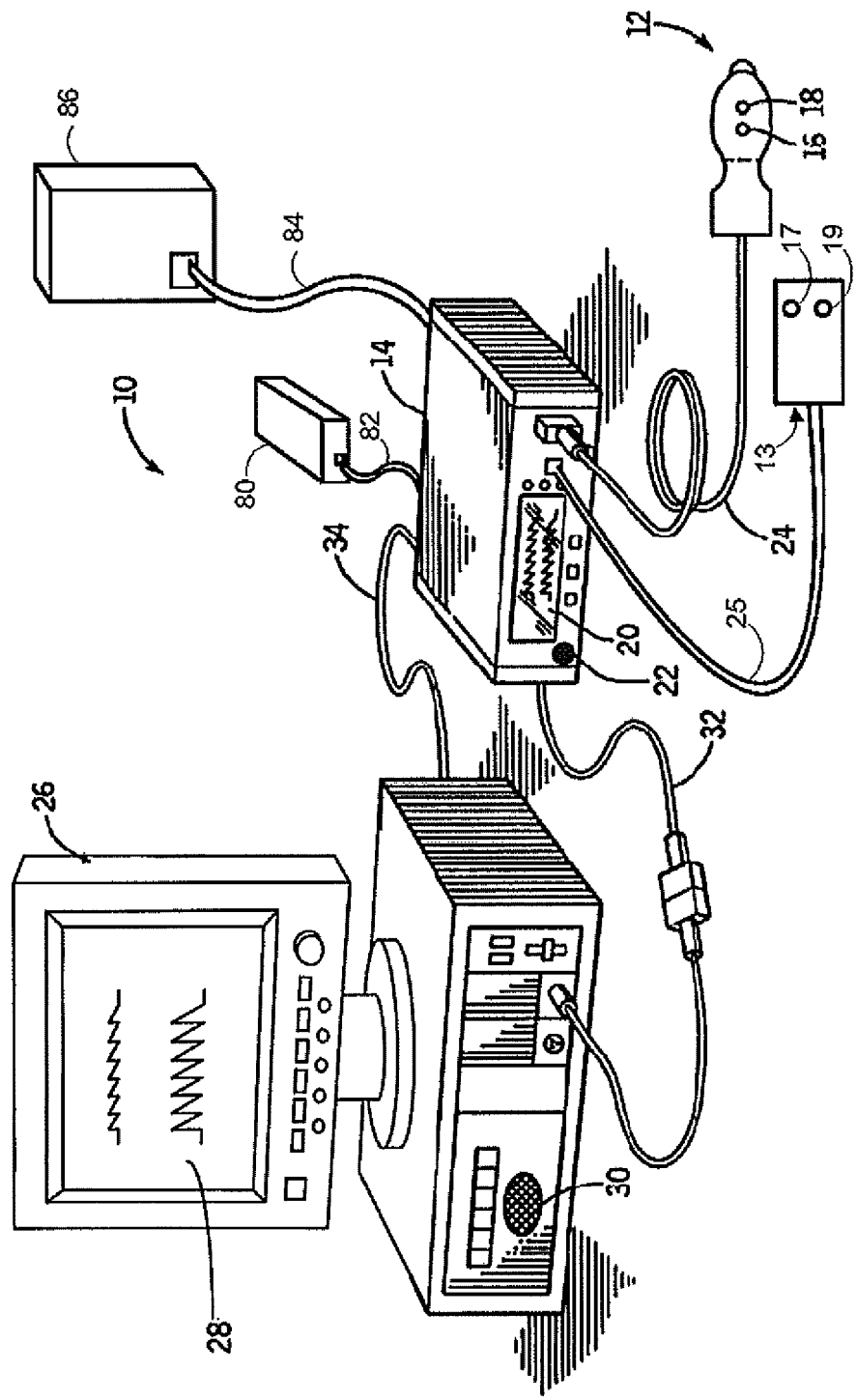
FIG. 1 shows an illustrative CNIBP monitoring system in accordance with an embodiment.

FIG. 1 is a perspective view of an embodiment of a CNIBP monitoring system 10 that may also be used to perform pulse oximetry. System 10 may include sensors 12 and 13 and a monitor 14. Sensor 12 may include an emitter 16 for emitting light at one or more wavelengths into a patient's tissue. A detector 18 may also be provided in sensor 12 for detecting the light originally from emitter 16 that emanates from the patient's tissue after passing through the tissue. Similarly, sensor 13 may include an emitter 17 and a detector 19, which may operate in a fashion similar to that of emitter 16 and detector 18, respectively.

Sensors 12 and 13 may be attached to different locations of a patient's body in order to measure values for time T in equation (1) above and thereby facilitate measurement of the patient's blood pressure. As an example, sensor 12 may be attached to the patient's finger, while sensor 13 may be attached to the patient's ear. It will be appreciated that other sensor locations may be used, as appropriate, and in an embodiment, only a single sensor or probe may be used.

According to an embodiment, emitter 16 and detector 18 may be on opposite sides of a digit such as a finger or toe, in which case the light that is emanating from the tissue has passed completely through the digit. In an embodiment, detector 18 (e.g., a reflective sensor) may be positioned anywhere a strong pulsatile flow may be detected (e.g., over arteries in the neck, wrist, thigh, ankle, ear, or any other suitable location). In an embodiment, emitter 16 and detector 18 may be arranged so that light from emitter 16 penetrates the tissue and is reflected by the tissue into detector 18, such as a sensor designed to obtain pulse oximetry or CNIBP data from a patient's forehead.

Similarly, according to an embodiment, emitter 17 and detector 19 may be on opposite sides of an ear (e.g., positioned on opposite sides of a patient's earlobe). In an embodiment, emitter 17 and detector 19 may be arranged so that light from emitter 17 penetrates the tissue and is reflected by the tissue into detector 19, such as a sensor designed to obtain pulse oximetry or CNIBP data from a patient's forehead.

According to another embodiment, system 10 may include a plurality of sensors forming a sensor array in lieu of either or both of sensors 12 and 13. Each of the sensors of the sensor array may be a complementary metal oxide semiconductor (CMOS) sensor. Alternatively, each sensor of the array may be a charged coupled device (CCD) sensor. In another embodiment, the sensor array may be made up of a combination of CMOS and CCD sensors. The CCD sensor may comprise a photoactive region and a transmission region for receiving and transmitting data whereas the CMOS sensor may be made up of an integrated circuit having an array of pixel sensors. Each pixel may have a photodetector and an active amplifier.

In an embodiment, the sensors or sensor array may be connected to and draw its power from monitor 14 as shown. In another embodiment, the sensors may be wirelessly connected to monitor 14 and may each include its own battery or similar power supply (not shown). Monitor 14 may be configured to calculate physiological parameters (e.g., blood pressure) based at least in part on data received from sensors 12 and 13 relating to light emission and detection. In an alternative embodiment, the calculations may be performed on the monitoring device itself and the result of the light intensity reading may be passed to monitor 14. Further, monitor 14 may include a display 20 configured to display the physiological parameters or other information about the system. In the embodiment shown, monitor 14 may also include a speaker 22 to provide an audible sound that may be used in various other embodiments, such as for example, sounding an audible alarm in the event that a patient's physiological parameters are not within a predefined normal range.

In an embodiment, sensors 12 and 13 may be communicatively coupled to monitor 14 via cables 24 and 25, respectively. However, in other embodiments, a wireless transmission device (not shown) or the like may be used instead of or in addition to either or both of cables 24 and 25.

In the illustrated embodiment, system 10 may also include a multi-parameter patient monitor 26. The monitor may be cathode ray tube type, a flat panel display (as shown) such as a liquid crystal display (LCD) or a plasma display, or any other type of monitor now known or later developed. Multi-parameter patient monitor 26 may be configured to calculate physiological parameters and to provide a display 28 for information from monitor 14 and from other medical monitoring devices or systems (not shown). For example, multi-parameter patient monitor 26 may be configured to display an estimate of a patient's blood pressure from monitor 14, blood oxygen saturation generated by monitor 14 (referred to as an "$SpO_2$" measurement), and pulse rate information from monitor 14.

Monitor 14 may be communicatively coupled to multi-parameter patient monitor 26 via a cable 32 or 34 that is coupled to a sensor input port or a digital communications port, respectively and/or may communicate wirelessly (not shown). In addition, monitor 14 and/or multi-parameter patient monitor 26 may be coupled to a network to enable the sharing of information with servers or other workstations (not shown). Monitor 14 may be powered by a battery (not shown) or by a conventional power source such as a wall outlet.

Calibration device 80, which may be powered by monitor 14, a battery, or by a conventional power source such as a wall outlet, may include any suitable blood pressure calibration device. For example, calibration device 80 may take the form of any invasive or non-invasive blood pressure monitoring or measuring system used to generate reference blood pressure measurements for use in calibrating the CNIBP monitoring techniques described herein. Such calibration devices may include, for example, an aneroid or mercury sphygmomanometer and occluding cuff, a pressure sensor inserted directly into a suitable artery of a patient, or any other device or mechanism used to sense, measure, determine, or derive a reference blood pressure measurement. In an embodiment, calibration device 80 may include a manual input device (not shown) used by an operator to manually input reference blood pressure measurements obtained from some other source (e.g., an external invasive or non-invasive blood pressure measurement system).

Calibration device 80 may also access reference blood pressure measurements stored in memory (e.g., RAM, ROM, or a storage device). For example, in an embodiment, calibration device 80 may access reference blood pressure measurements from a relational database stored within calibration device 80, monitor 14, or multi-parameter patient monitor 26. As described in more detail below, the reference blood pressure measurements generated or accessed by calibration device 80 may be updated in real-time, resulting in a continuous source of reference blood pressure measurements for use in continuous or periodic calibration. Alternatively, reference blood pressure measurements generated or accessed by calibration device 80 may be updated periodically, and calibration may be performed on the same periodic cycle. In the depicted embodiments, calibration device 80 is connected to monitor 14 via cable 82. In other embodiments, calibration device 80 may be a stand-alone device that may be in wireless communication with monitor 14. In still other embodiments, calibration device 80 is completely integrated within monitor 14.

Figure 2:
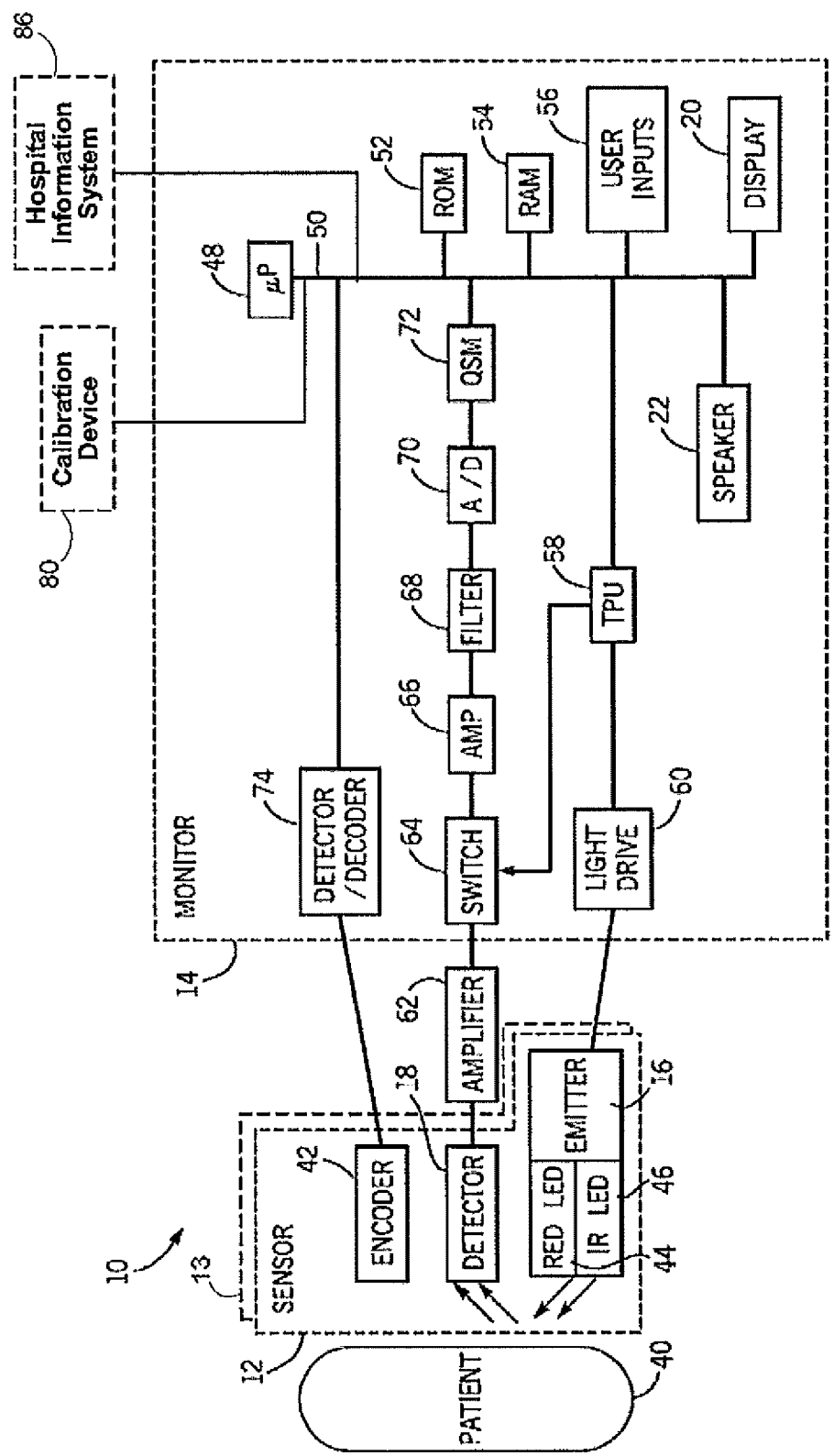
FIG. 2 is a block diagram of the illustrative CNIBP monitoring system of FIG. 1 coupled to a patient in accordance with an embodiment.

FIG. 2 is a block diagram of a CNIBP monitoring system, such as system 10 of FIG. 1, which may be coupled to a patient 40 in accordance with an embodiment. Certain illustrative components of sensors 12 and 13 and monitor 14 are illustrated in FIG. 2. Because sensors 12 and 13 may include similar components and functionality, only sensor 12 will be discussed in detail for ease of illustration. It will be understood that any of the concepts, components, and operation discussed in connection with sensor 12 may be applied to sensor 13 as well (e.g., emitter 16 and detector 18 of sensor 12 may be similar to emitter 17 and detector 19 of sensor 13). Similarly, it will be understood that, as discussed in connection with FIG. 1, certain embodiments may use only a single sensor or probe, instead of a plurality of sensors or probes as illustrated in FIG. 2.

Sensor 12 may include emitter 16, detector 18, and encoder 42. In the embodiment shown, emitter 16 may be configured to emit at least one wavelength of light (e.g., RED or IR) into a patient's tissue 40. For calculating $SpO_2$, emitter 16 may include a RED light emitting light source such as RED light emitting diode (LED) 44 and an IR light emitting light source such as IR LED 46 for emitting light into the patient's tissue 40. In other embodiments, emitter 16 may include a light emitting light source of a wavelength other than RED or IR. In one embodiment, the RED wavelength may be between about 600 nm and about 700 nm, and the IR wavelength may be between about 800 nm and about 1000 nm. In embodiments where a sensor array is used in place of single sensor, each sensor may be configured to emit a single wavelength. For example, a first sensor emits only a RED light while a second only emits an IR light.

It will be understood that, as used herein, the term "light" may refer to energy produced by radiative sources and may include one or more of ultrasound, radio, microwave, millimeter wave, infrared, visible, ultraviolet, gamma ray or X-ray electromagnetic radiation. As used herein, light may also include any wavelength within the radio, microwave, infrared, visible, ultraviolet, or X-ray spectra, and that any suitable wavelength of electromagnetic radiation may be appropriate for use with the present techniques. Detector 18 may be chosen to be specifically sensitive to the chosen targeted energy spectrum of the emitter 16.

In an embodiment, detector 18 may be configured to detect the intensity of light at the emitted wavelengths (or any other suitable wavelength). Alternatively, each sensor in the array may be configured to detect an intensity of a single wavelength. In operation, light may enter detector 18 after passing through the patient's tissue 40. Detector 18 may convert the intensity of the received light into an electrical signal. The light intensity is directly related to the absorbance and/or reflectance of light in the tissue 40. That is, when more light at a certain wavelength is absorbed or reflected, less light of that wavelength is received from the tissue by the detector 18. After converting the received light to an electrical signal, detector 18 may send the signal to monitor 14, where physiological parameters may be calculated based on the absorption of one or more of the RED and IR (or other suitable) wavelengths in the patient's tissue 40.

In an embodiment, encoder 42 may contain information about sensor 12, such as what type of sensor it is (e.g., whether the sensor is intended for placement on a forehead or digit) and the wavelength or wavelengths of light emitted by emitter 16. This information may be used by monitor 14 to select appropriate algorithms, lookup tables and/or calibration coefficients stored in monitor 14 for calculating the patient's physiological parameters.

Encoder 42 may contain information specific to patient 40, such as, for example, the patient's age, weight, and diagnosis. This information may allow monitor 14 to determine, for example, patient-specific threshold ranges in which the patient's physiological parameter measurements should fall and to enable or disable additional physiological parameter algorithms. Encoder 42 may, for instance, be a coded resistor which stores values corresponding to the type of sensor 12 or the type of each sensor in the sensor array, the wavelength or wavelengths of light emitted by emitter 16 on each sensor of the sensor array, and/or the patient's characteristics. In another embodiment, encoder 42 may include a memory on which one or more of the following information may be stored for communication to monitor 14: the type of the sensor 12; the wavelength or wavelengths of light emitted by emitter 16; the particular wavelength each sensor in the sensor array is monitoring; a signal threshold for each sensor in the sensor array; any other suitable information; or any combination thereof.

In an embodiment, signals from detector 18 and encoder 42 may be transmitted to monitor 14. In the embodiment shown, monitor 14 may include a general-purpose microprocessor 48 connected to an internal bus 50. Microprocessor 48 may be adapted to execute software, which may include an operating system and one or more applications, as part of performing the functions described herein. Also connected to bus 50 may be a read-only memory (ROM) 52, a random access memory (RAM) 54, user inputs 56, display 20, and speaker 22.

RAM 54 and ROM 52 are illustrated by way of example, and not limitation. Any suitable computer-readable media may be used in the system for data storage. Computer-readable media are capable of storing information that can be interpreted by microprocessor 48. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system.

In the embodiment shown, a time processing unit (TPU) 58 may provide timing control signals to a light drive circuitry 60, which may control when emitter 16 is illuminated and multiplexed timing for the RED LED 44 and the IR LED 46. TPU 58 may also control the gating-in of signals from detector 18 through an amplifier 62 and a switching circuit 64. These signals are sampled at the proper time, depending upon which light source is illuminated. The received signal from detector 18 may be passed through an amplifier 66, a low pass filter 68, and an analog-to-digital converter 70. The digital data may then be stored in a queued serial module (QSM) 72 (or buffer) for later downloading to RAM 54 as QSM 72 fills up. In one embodiment, there may be multiple separate parallel paths having amplifier 66, filter 68, and A/D converter 70 for multiple light wavelengths or spectra received.

In an embodiment, microprocessor 48 may determine the patient's physiological parameters, such as blood pressure, $SpO_2$, and pulse rate, using various algorithms and/or look-up tables based on the value of the received PPG signals and/or data corresponding to the light received by detector 18. Signals corresponding to information about patient 40, and particularly about the intensity of light emanating from a patient's tissue over time, may be transmitted from encoder 42 to a decoder 74. These signals may include, for example, encoded information relating to patient characteristics. Decoder 74 may translate these signals to enable the microprocessor to determine the thresholds based on algorithms or look-up tables stored in ROM 52. User inputs 56 may be used to enter information about the patient, such as age, weight, height, diagnosis, medications, treatments, and so forth. In an embodiment, display 20 may exhibit a list of values which may generally apply to the patient, such as, for example, age ranges or medication families, which the user may select using user inputs 56.

The optical signal through the tissue can be degraded by noise, among other sources. One source of noise is ambient light that reaches the light detector, Another source of noise is electromagnetic coupling from other electronic instruments. Movement of the patient also introduces noise and affects the signal. For example, the contact between the detector and the skin, or the emitter and the skin, can be temporarily disrupted when movement causes either to move away from the skin. In addition, because blood is a fluid, it responds differently than the surrounding tissue to inertial effects, thus resulting in momentary changes in volume at the point to which the sensor or probe is attached.

Noise (e.g., from patient movement) can degrade a CNIBP or pulse oximetry signal relied upon by a physician, without the physician's awareness. This is especially true if the monitoring of the patient is remote, the motion is too small to be observed, or the doctor is watching the instrument or other parts of the patient, and not the sensor site. Processing CNIBP or pulse oximetry (i.e., PPG) signals may involve operations that reduce the amount of noise present in the signals or otherwise identify noise components in order to prevent them from affecting measurements of physiological parameters derived from the PPG signals.

In an embodiment, microprocessor 48 may be operable to receive data relating to detected PPG signals, computed blood pressure measurements, sensor elevation, or any other suitable data for use in determining whether monitor 14 should be recalibrated or its signal normalized. For example, microprocessor 48 may receive reference blood pressure measurements from calibration device 80, which may be coupled to microprocessor 48 through bus 50. Additionally, microprocessor 48 may receive patient data from hospital information system 86 through bus 50 that may indicate a need for signal normalization or recalibration, such as data relating to expected drug administrations, medical procedures, or medical equipment.

Figure 3:
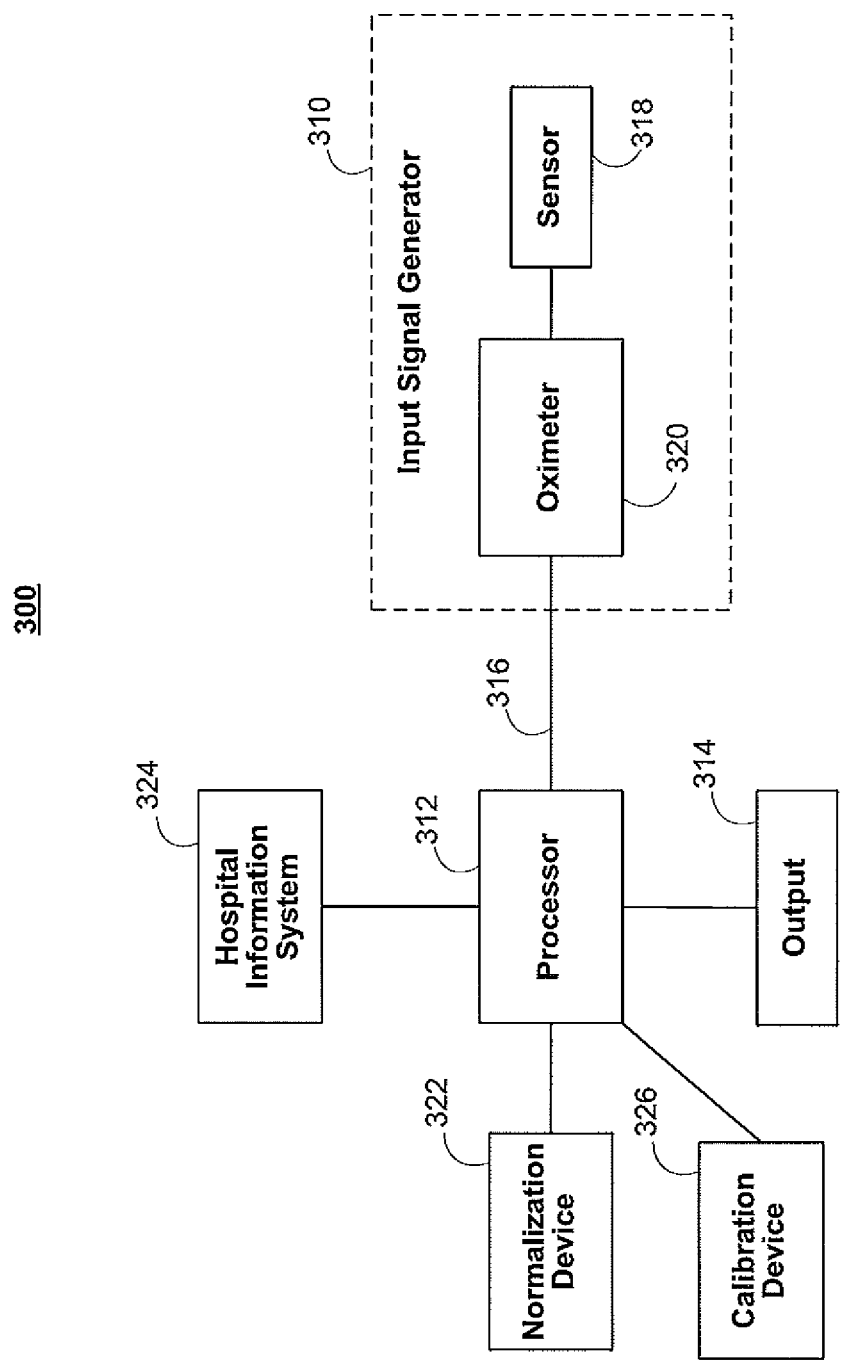
FIG. 3 is a block diagram of an illustrative signal processing system in accordance with an embodiment.

FIG. 3 is an illustrative processing system 300 in accordance with an embodiment. In this embodiment, input signal generator 310 generates an input signal 316. As illustrated, input signal generator 310 may include oximeter 320 (or similar device) coupled to sensor 318, which may provide as input signal 316 a PPG signal. It will be understood that input signal generator 310 may include any suitable signal source, signal generating data, signal generating equipment, or any combination thereof to produce signal 316. Additionally, input signal generator 310 may in some embodiments include more than one sensor 318.

In this embodiment, signal 316 may be coupled to processor 312. Processor 312 may be any suitable software, firmware, and/or hardware, and/or combinations thereof for processing signal 316. For example, processor 312 may include one or more hardware processors (e.g., integrated circuits), one or more software modules, computer-readable media such as memory, firmware, or any combination thereof. Processor 312 may, for example, be a computer or may be one or more chips (i.e., integrated circuits). Processor 312 may perform some or all of the calculations associated with the blood pressure monitoring methods of the present disclosure. For example, processor 312 may determine the time difference, T, between any two chosen characteristic points of a PPG signal obtained from input signal generator 310. As another example, if input signal generator contains more than one sensor 318, processor 312 may determine the time difference, T, required for a PPG signal to travel from one sensor 318 to another. Processor 312 may also be configured to apply equation (1) (or any other blood pressure equation using an elapsed time value) and compute estimated blood pressure measurements on a continuous or periodic basis. Processor 312 may also perform any suitable signal processing of signal 316 to filter signal 316, such as any suitable band-pass filtering, adaptive filtering, closed-loop filtering, and/or any other suitable filtering, and/or any combination thereof. For example, signal 316 may be filtered one or more times prior to or after identifying characteristic points in signal 316.

Processor 312 may be coupled to one or more memory devices (not shown) or incorporate one or more memory devices such as any suitable volatile memory device (e.g., RAM, registers, etc.), non-volatile memory device (e.g., ROM, EPROM, magnetic storage device, optical storage device, flash memory, etc.), or both. Processor 312 may be coupled to normalization device 322 that may be used to normalize PPG signals for use in CNIBP calculations. Processor 312 may additionally be coupled to hospital information system 324, which may store and transmit direct information indicative of a need for normalization. Processor 312 may perform normalization of CNIBP measuring system and the PPG signal using information received from input signal generator 310, normalization device 322, hospital information system 324, calibration device 326 or any other suitable device.

Processor 312 may be coupled to output 314. Output 314 may be any suitable output device such as, for example, one or more medical devices (e.g., a medical monitor that displays various physiological parameters, a medical alarm, or any other suitable medical device that either displays physiological parameters or uses the output of processor 212 as an input), one or more display devices (e.g., monitor, PDA, mobile phone, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

It will be understood that system 300 may be incorporated into system 10 (FIGS. 1 and 2) in which, for example, input signal generator 310 may be implemented as parts of sensors 12 and 13 and monitor 14 and processor 312 may be implemented as part of monitor 14. In an embodiment, portions of system 300 may be configured to be portable. For example, all or a part of system 300 may be embedded in a small, compact object carried with or attached to the patient (e.g., a watch (or other piece of jewelry) or cellular telephone). In such embodiments, a wireless transceiver (not shown) may also be included in system 300 to enable wireless communication with other components of system 10. As such, system 10 may be part of a fully portable and continuous blood pressure monitoring solution.

According to the present disclosure, reliable blood pressure measurements may be derived substantially continuously using PPG signals which may require normalization in response to servoing, gain changes, or other change to the PPG signal. The present disclosure may be applied to measuring systolic blood pressure, diastolic blood pressure, mean blood pressure, or any combination thereof on an on-going, continuous, or periodic basis.

In an embodiment, reliable blood pressure measurements may be derived from a PPG signal obtained from a single sensor or probe, or from multiple PPG signals obtained from multiple sensors or probes. In an embodiment, the constants a and b in equation (1) above may be determined by performing an initial calibration. The calibration may involve taking a reference blood pressure reading to obtain a reference blood pressure $P_0$, measuring the elapsed time $T_0$ corresponding to the reference blood pressure, and then determining values for both of the constants a and b from the reference blood pressure and elapsed time measurement. Calibration may be performed at any suitable time (e.g., once initially after monitoring begins) or on any suitable schedule (e.g., a periodic or event-driven schedule). Normalization of the PPG signal may be performed in order to avoid unnecessary calibration.

In an embodiment, the calibration may include performing calculations mathematically equivalent to $$a = c_1 + \frac{c_2(P_0 - c_1)}{\ln(T_0) + c_2} \quad (2)$$

and $$b = \frac{P_0 - c_1}{\ln(T_0) + c_2} \quad (3)$$

to obtain values for the constants a and b, where $c_1$ and $c_2$ are predetermined constants that may be determined, for example, based on empirical data.

In other embodiments, determining the plurality of constant parameters in the multi-parameter equation (1) may include performing calculations mathematically equivalent to $$a = P_0 - (c_3 T_0 + c_4)\ln(T_0) \quad (4)$$

and $$b = c_3 T_0 + c_4 \quad (5)$$

where a and b are first and second parameters and $c_3$ and $c_4$ are predetermined constants that may be determined, for example, based on empirical data.

In an embodiment, the multi-parameter equation (1) may include a non-linear function which is monotonically decreasing and concave upward in a manner specified by the constant parameters.

Figure 5A:
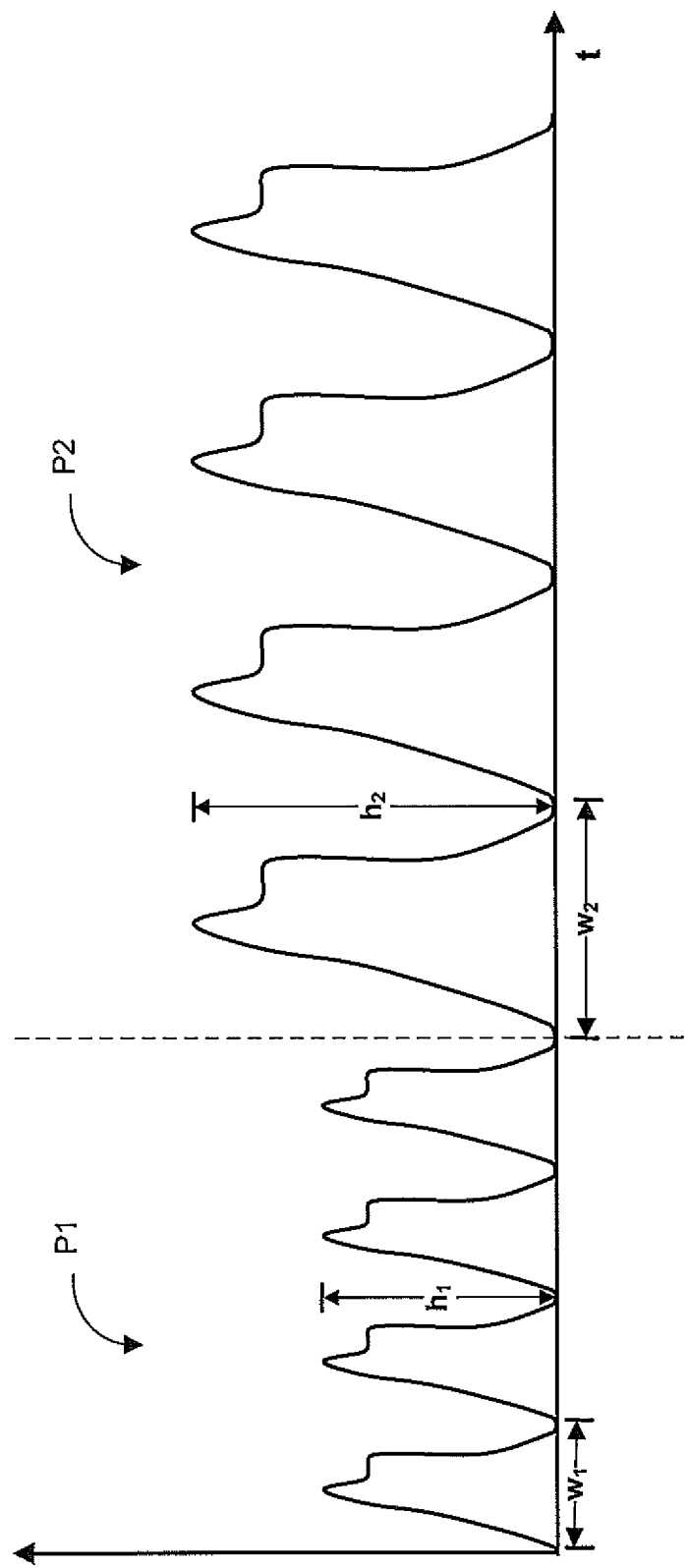
FIGS. 5A-B and 6 show illustrative PPG signals in accordance with an embodiment.
Figure 5B:
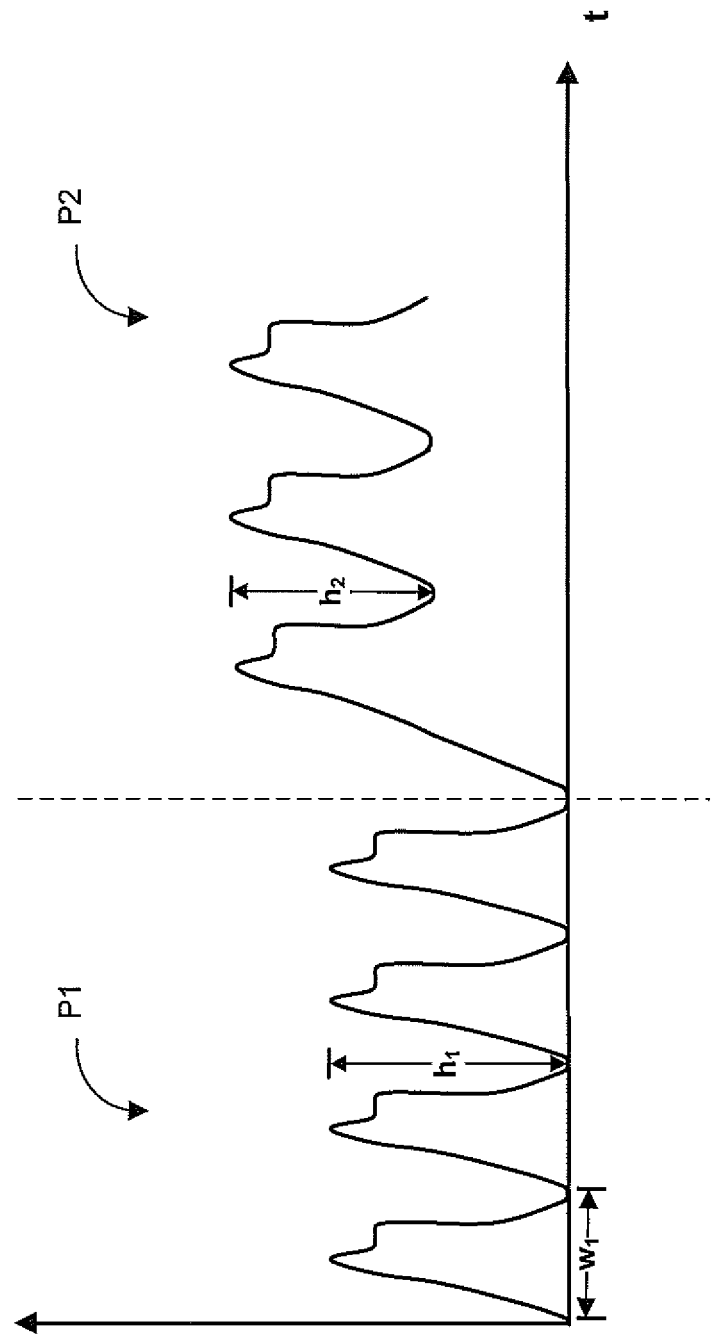
Figure 6:
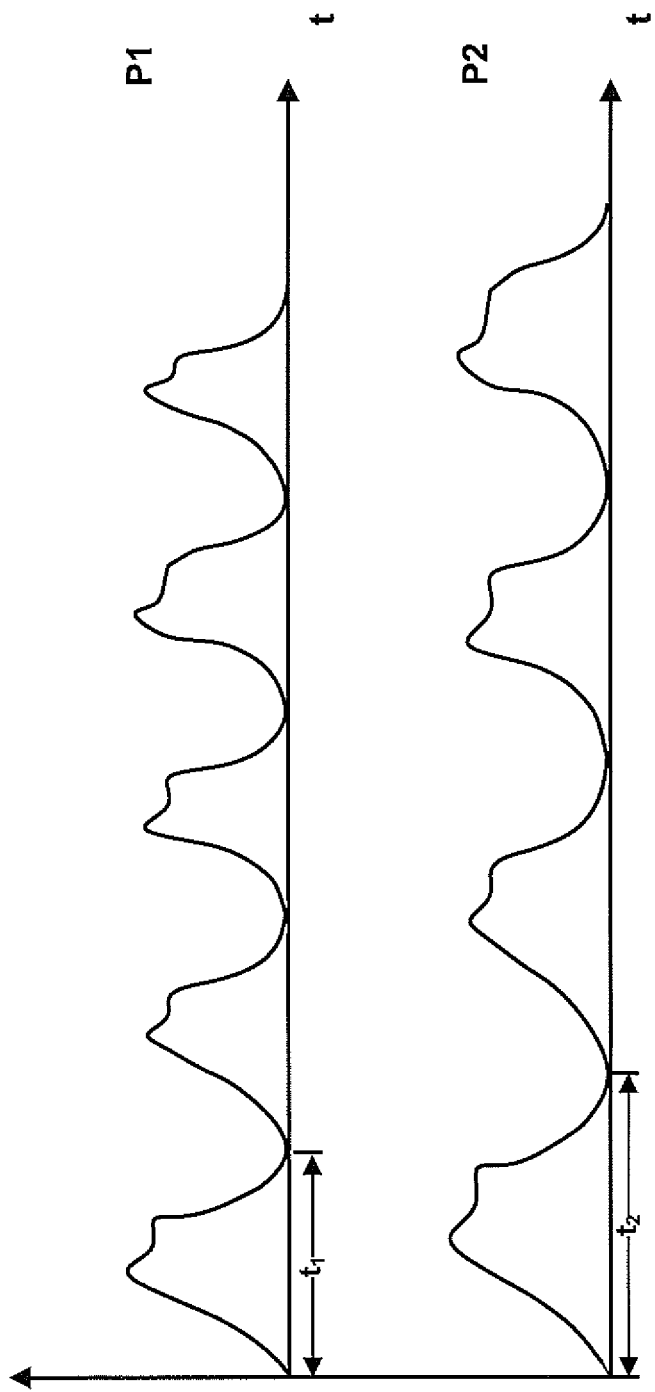

In an embodiment, normalization of a PPG signal may be performed using one or more, or combinations of the following techniques: area scaling, amplitude scaling, pulse period scaling, as further described with reference to FIGS. 5A-B and 6. In an embodiment, the amplitudes can be scaled based on DC changes of a PPG signal. The normalizing of a PPG signal may be provided using linear or nonlinear resealing of a pulse (AC) component depending, for example, on whether the DC and AC component are linearly or nonlinearly related. Each of these techniques are further described herein. In an embodiment, normalizing of the PPG signal may be provided on a continuous basis. In another embodiment, normalizing of the PPG signal may be performed when metrics associated with the PPG signal at two different times differ by more than a threshold.

As described above, in an embodiment a PPG signal may be generated by a pulse oximeter or similar device positioned at any suitable location of a subject's body. Additionally, a PPG signal may be generated at each of a plurality of locations of a subject's body, with at least one probe or sensor attached to each location. The time difference T that it takes for a pulse in a PPG signal to appear at one location and another location (e.g., at a patient's ear and at the patient's finger or toe) may then be measured and used to derive a blood pressure measurement for the patient using a calibrated version of equation (1) or using any other relationship, such as lookup tables and the like. Time T may be measured, for example, by determining the difference between how long it takes for a given characteristic point, observed in the PPG signal at the first sensor or probe location, to appear in the PPG signal at the second sensor or probe location.

In an embodiment, a PPG signal may be generated using only a single sensor or probe attached to the subject's body. In such a scenario, the time difference, T, may correspond to the time it takes the pulse wave to travel a predetermined distance (e.g., a distance from the sensor or probe to a reflection point and back to the sensor or probe). Characteristic points in the PPG signal may include the time between various peaks in the PPG signal and/or in some derivative of the PPG signal. For example, in an embodiment, the time difference, T, may be calculated between (1) the maximum peak of the PPG signal in the time domain and the second peak in the 2nd derivative of the PPG signal (the first 2nd derivative peak may be close to the maximum peak in the time domain) and/or (2) peaks in the 2nd derivative of the PPG signal. Any other suitable time difference between any suitable characteristic points in the PPG signal or any derivative of the PPG signal may be used as T in other embodiments.

In an embodiment, the time difference between the adjacent peaks in the PPG signal, the time difference between the adjacent valleys in the PPG signal, or the time difference between any combination of peaks and valleys, can be used as the time difference T. As such, adjacent peaks and/or adjacent valleys in the PPG signal (or in any derivative thereof) may also be considered characteristic points. In an embodiment, these time differences may be divided by the actual or estimated heart rate to normalize the time differences. In an embodiment, the resulting time difference values between two peaks may be used to determine the systolic blood pressure, and the resulting time difference values between two valleys may be used to determine the diastolic blood pressure.

In an embodiment, blood pressure may be determined by, for example, measuring the area under a pulse or a portion of the pulse in the PPG signal. These measurements may be correlated with empirical blood pressure data (corresponding to previous blood pressure measurements of the patient or one or more other patients) to determine the blood pressure. In some implementations, the blood pressure may be determined by looking up the area measurement values in a table, which may be stored in a memory, to obtain corresponding blood pressures. Alternatively, the blood pressure may be determined by using any suitable blood pressure-area mapping equation which is generated based on blood pressure and area measurements associated with one or more patients. For example, measured samples may be plotted in a graph that maps blood pressure to area. The graph may be analyzed to generate a linear-best-fit-line approximation, non-linear best fit line approximation or other suitable approximation from which to derive an equation that may be used to determine blood pressure by providing an area measurement.

As shown in FIG. 4, the top plot (A) depicts a raw PPG signal 400A which shows a relatively consistent baseline in section 410. At point 420, the baseline changes and leads to an increased baseline in section 430 at approximately −75. The middle plot (B) of FIG. 4 depicts a filtered PPG signal 400B. The lower plot (C) of FIG. 4 depicts normalized filtered PPG signal 400C. As can be seen, normalizing and filtering the signal leads to a more consistent plot in sections 410 and 430 for signal 400C, than that of the raw data signal 400A.

In an embodiment, section 410 depicts a PPG signal for a CNIBP system. At point 420 a change in the PPG signal may have occurred as a result of a change in the monitoring device. For example, a sensor setting in sensor 12 (FIG. 1), may have occurred, such as, an emitter change (e.g., an LED drive current change), a detector change (e.g., a gain change), an amplifier gain change, or any other sensor or monitor related setting change. The change at point 420 may have been triggered by a light optimization routine performed by processor 312 (FIG. 3). The resulting change in the PPG signal may cause a CNIBP system to trigger a recalibration event even though no underlying change in a monitored patient or the CNIBP system has occurred, other than a sensor setting change. For example, a recalibration event may be triggered based at least in part on characteristics of the PPG signal (e.g., amplitude, period, area, and/or slope characteristics). In order to avoid such a recalibration event, the PPG signal may be normalized, for example, as shown in plot (C) before determining whether to trigger a recalibration.

Normalization of the PPG signal may be performed using one or more techniques alone or in combination. For example, the PPG signal may be resealed using a monitor or sensor setting change (e.g., an AC or DC drive current setting of an emitter). Resealing the PPG signal using the monitor or sensor setting change may be provided using processor 312 (FIG. 3) which may obtain the current setting information from signal generator 310 (FIG. 3) or sensor 12 (FIG. 1) and monitor 14 (FIG. 2) used in the light optimization of the wavelength used by the sensor 12 (FIG. 1). In other embodiments, the monitor sensor setting change information may be obtained from other sources, or be manually entered, e.g., using user input 56 (FIG. 2).

Another normalization technique may be scaling of a peak to peak amplitude to a given number (e.g., unity). Scaling of a peak to peak amplitude may comprise conforming the amplitude of a PPG signal following a monitor or sensor setting change to the amplitude of the PPG signal prior to the change to produce a conforming PPG signal. Turning to FIG. 5A a PPG signal P1 is depicted having an average or mean amplitude $h_1$ (prior to a monitor or sensor change). The PPG signal section P1 changes amplitude following a monitor or sensor setting change (or other change) as shown in section P2, which has an average or mean amplitude height of $h_2$. By scaling the amplitude of PPG signal section P2 to the amplitude of signal section P1 using the respective heights $h_1$ and $h_2$, the PPG signal can be normalized. In another embodiment, amplitude scaling may be used to scale the amplitudes of P2 and P1 to another given amplitude. Scaling of the PPG signal may be performed, for example, by processor 312 (FIG. 3) or normalization device 322 (FIG. 3).

Another normalization technique may use an area of a pulse. An area normalization technique may use the area of a shape under the PPG signal, for example, the PPG signal sections P1 and P2 of FIG. 5A. The area under the PPG signal P1 and P2 may be scaled to create a normalized PPG signal. In such a calculation, the amplitudes $h_1$ and $h_2$ may be forced to scale, along with the widths $w_1$ and $w_2$. The height and width of a pulse may be scaled proportionally to each other or the height or width may be scaled greater than the other. In an embodiment, area scaling may be used to scale the areas of P2 and P1 to another given area (e.g., unity). The PPG signal may also be normalized using a ratio of an area of a PPG signal shape. For example, a ratio may be obtained for the area of the shape under the signal in section P1 (i.e., before the change) and the area of the shape under the signal in section P2 (i.e., after the change). The resulting ratio value may then be used to obtain a normalized PPG signal. Such calculations, ratios, and scaling of the PPG signal may be performed by processor 312 (FIG. 3) or normalization device 322 (FIG. 3).

Another technique may include using baseline changes for scaling a PPG signal. In FIG. 5B, a change in a PPG signal occurs causing a different baseline for PPG signal sections P1 and P2, which have different heights $h_1$ and $h_2$. The difference in baselines of the signals may be used to normalize signal P2. In FIG. 5B, the vertical axis represents a decrease in light received. In a linear system, if the baseline doubles, the amplitude of the pulses may be halved. By doubling the pulse amplitude, the signal may be normalized. In a non-linear system, the amplitudes may be scaled using a function of the non-linear equation relating baseline and amplitude. Accordingly, changes in the baseline may be monitored and used to scale the pulse amplitudes.

Another technique may include measuring a period or time difference between first and second features of the PPG signals to normalize the signals. A time difference between adjacent peaks in the PPG signal, the time difference between the adjacent valleys in the PPG signal, or the time difference between any combination of peaks and valleys or other characteristic features of a pulse, can be used as the time difference T. In an embodiment, these time differences may be used to normalize time differences in PPG signals. For example, the representative PPG signals P1 and P2 shown in FIG. 6 are PPG signals having a different periods or time differences $t_1$ and $t_2$. P2 may be normalized by scaling $t_2$ for each pulse to $t_1$. In another embodiment, pulse period scaling may be used to scale the pulse period of P2 and P1 to another given period (e.g., unity). This and other normalization techniques may be performed by processor 312 (FIG. 3), normalization device 322 (FIG. 3), or other combination of devices.

Figure 7:
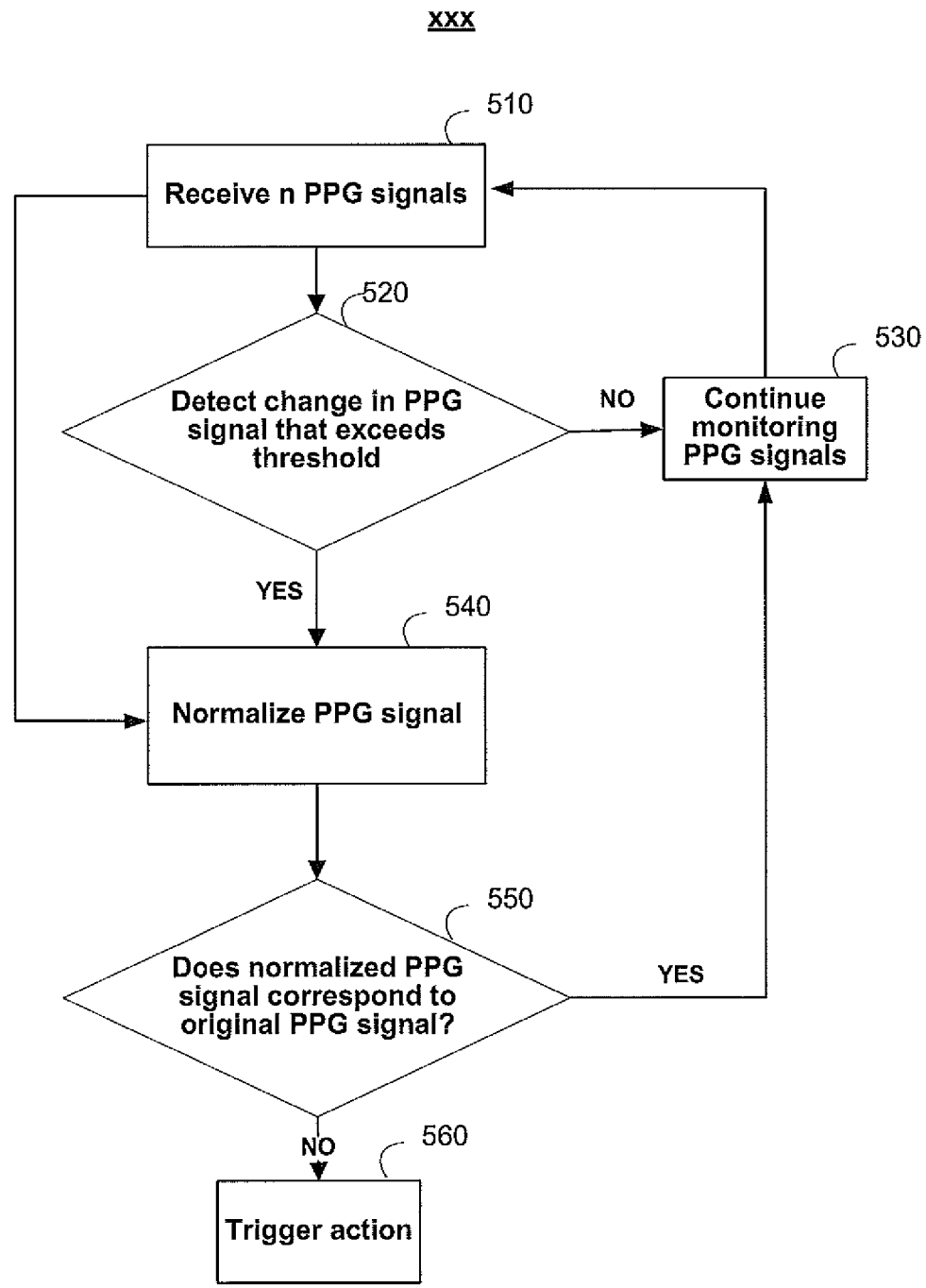
FIG. 7 shows an illustrative process for normalizing a PPG signal in accordance with an embodiment.

In an embodiment, analysis of a PPG signal in patient monitoring may be provided using the steps of the flowchart depicted in FIG. 7. As shown, a PPG signal may be received at step 510. In an embodiment, the PPG signal may be received from sensor 12 or 13 (FIG. 1) which is being used to monitor a patient. Sensor 12 or 13 (FIG. 1) may be a component that provides continuous readings in a CNIBP system, and provides continuous blood pressure measurements, continuous blood oxygen saturation measurements, and or other measurements on a continuous basis. Aspects of the PPG signal may be based on reference information manually entered using user input component 56 (FIG. 2), encoder 42 (FIG. 2) or other suitable component. In a continuous patient monitoring scenario the PPG signal may be any signal received over a period of time that may be received from, for example, sensors 12 or 13 (FIG. 1) and analyzed and processed using processor 312 (FIG. 3). Processor 312 (FIG. 3) may be configured to continuously or periodically monitor received PPG signals.

At step 520 a change may be detected in the PPG signal. The change may be detected using the processor 312 (FIG. 3) to analyze received PPG signal(s) to detect whether any changes or differences exists in the PPG signal over time. For example, changes in one or more of the following characteristics of the PPG signal may be analyzed: pulse amplitude, pulse period, time difference between characteristic points within or between pulses, pulse area, the slope of one or more sections of a pulse, rise time, fall time, baseline, or any other suitable characteristic. In general, a range of values, or certain thresholds may be established for use in identifying a significant deviation in signals. The range of values or threshold may be stored in processor 312 (FIG. 3) accessible memory. Such values and thresholds may be stored in a relational database for particular types of physiological parameters and also for certain patient criteria. The range of values and threshold may be selectably entered using user input component 56 (FIG. 2) or encoder 42 (FIG. 2). In an embodiment, the change may also be detected by receipt of a signal indicating that a gain change or other monitor or sensor change has occurred. If no difference or deviation in the PPG signal that exceeds the range of values of threshold is detected at step 520, continuous monitoring may continue at step 530 and loop back to step 510. If a difference is detected at step 520, a normalization procedure for the PPG signal may be performed at step 540 using, for example, processor 312 (FIG. 3). In an embodiment, normalization at step 540 may be performed on a continuous basis without determining whether any thresholds have been exceeded at step 520.

Examples of normalization procedures have been discussed herein, such as peak to peak amplitude scaling of a PPG signal, area scaling of a pulse, pulse period scaling, and baseline scaling. Normalization procedures, such as pulse period scaling and peak to peak amplitude, as well as combinations thereof may be used to prevent changes in heart rate from triggering a recalibration due to changes in a measured metric, such as changes in a pulse wave area.

Following normalization of the PPG signal at step 540, circuitry, such as processor 312 (FIG. 3), may determine whether the normalized PPG signal corresponds to the original PPG signal at step 550. Lower plot (C) (FIG. 4), for example, shows a normalized PPG signal that may be substantially similar to a prior signal. If the normalized PPG signal is determined to correspond to the prior PPG signal, monitoring of the PPG signals may continue at step 530. In general, the same range of values and thresholds used in step 520 may be used at step 550. Optionally, other sets of values may be used for a comparison of the normalized PPG signal. If the normalized PPG signal does not correspond to the prior PPG signal, an action may trigger at step 560. The action may be triggered by processor 312 (FIG. 3) transmitting a signal to another system component to perform an action. Some examples of triggered actions may include a recalibration operation or an alarm. For example, processor 312 (FIG. 3) may issue a recalibration signal to monitor 14 (FIG. 2), or an alarm signal to display 28 (FIG. 1) or speaker 22 (FIG. 1).

The foregoing is merely illustrative of the principles of this disclosure and various modifications can be made by those skilled in the art without departing from the scope and spirit of the disclosure. The above described embodiments are presented for purposes of illustration and not of limitation. The present disclosure also can take many forms other than those explicitly described herein. Accordingly, it is emphasized that the disclosure is not limited to the explicitly disclosed methods, systems, and apparatuses, but is intended to include variations to and modifications thereof which are within the spirit of the following claims.

What is claimed is:

1. A method for normalizing a signal using a continuous non-invasive blood pressure monitoring system, comprising:
   detecting a photoplethysmograph (PPG) signal at a first time and a second time with a sensor coupled to a processor;
   determining, using the processor, whether a difference in a metric of the PPG signal at the first time and a metric of the PPG signal at the second time exceeds a threshold;
   normalizing the PPG signal at the second time when the threshold is determined to be exceeded;
   comparing, using the processor, the normalized PPG signal and the PPG signal at the first time; and
   generating a signal, using the processor, if the normalized PPG signal and the PPG signal at the first time do not correspond.

2. The method of claim 1 wherein normalizing, using the processor, the signal at the second time comprises a calculation based at least in part on a change in amplitude, area, pulse period, baseline, or any combination thereof.

3. The method of claim 1 wherein the signal indicates: an alarm, a request to perform a recalibration operation, or a combination thereof.

4. The method of claim 1 further comprising detecting a second PPG signal with a second sensor.

5. The method of claim 1 wherein the PPG signal is capable of being used to calculate blood pressure, blood oxygen saturation, or a combination thereof.

6. The method of claim 1 wherein the metric of the PPG signal at the first time and the metric of the PPG signal at the second time comprises: peak amplitude, area, period, baseline, or any combination thereof.

7. A system for analyzing photoplethysmograph (PPG) signals in patient monitoring, comprising:
   a sensor having at least one emitter and at least one detector configured to detect a PPG signal, the sensor coupled to a processor, the processor capable of:
   detecting a PPG signal at a first time and a second time with the sensor;
   determining whether a difference in a metric of the PPG signal at the first time and a metric of the PPG signal at the second time exceeds a threshold;

normalizing the PPG signal at the second time when the threshold is determined to be exceeded;
comparing the normalized PPG signal and the PPG signal at the first time; and
generating a signal if the normalized PPG signal and the PPG signal at the first time do not correspond.

8. The system of claim 7 wherein the normalizing the PPG at the second time comprises a calculation based at least in part on a change in amplitude, area, pulse period, baseline, or any combination thereof.

9. The system of claim 7 wherein the signal indicates: an alarm, a request to perform a recalibration operation, or a combination thereof.

10. The system of claim 7 further comprising a second sensor having at least one emitter and at least one detector configured to detect a second PPG signal, the second sensor coupled to the processor.

11. The system of claim 7 wherein the PPG signal is capable of being used to calculate blood pressure, blood oxygen saturation, or a combination thereof.

12. The system of claim 7 wherein the metric of the PPG signal at the first time and the metric of the PPG signal at the second time comprises: peak amplitude, area, period, baseline, or any combination thereof.

* * * * *